(12) United States Patent
Hotter et al.

(10) Patent No.: US 8,946,441 B2
(45) Date of Patent: Feb. 3, 2015

(54) POLYMORPHS OF AN ACTIVE PHARMACEUTICAL INGREDIENT

(75) Inventors: Andreas Hotter, Kundl (AT); Ulrich Griesser, Innsbruck (AT); Verena Adamer, Innsbruck (AT); Christoph Langes, Innsbruck (AT)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 13/702,077

(22) PCT Filed: Jun. 24, 2011

(86) PCT No.: PCT/EP2011/161245
§ 371 (c)(1),
(2), (4) Date: Feb. 14, 2013

(87) PCT Pub. No.: WO2011/161245
PCT Pub. Date: Dec. 29, 2011

(65) Prior Publication Data
US 2013/0137734 A1 May 30, 2013

(30) Foreign Application Priority Data
Jun. 25, 2010 (EP) .................................. 10167344

(51) Int. Cl.
C07D 277/00 (2006.01)
A61K 31/425 (2006.01)
C07D 277/56 (2006.01)

(52) U.S. Cl.
CPC .................................. *C07D 277/56* (2013.01)
USPC .......................................... 548/201; 514/365

(58) Field of Classification Search
USPC .......................................... 548/201; 514/365
See application file for complete search history.

(56) References Cited

U.S. PATENT DOCUMENTS

| 6,225,474 B1 * | 5/2001 | Matsumoto et al. ........... 548/201 |
| 7,361,676 B2 * | 4/2008 | Iwai et al. ..................... 514/365 |
| 2005/0043375 A1 | 2/2005 | Iwai et al. |
| 2010/0317702 A1 * | 12/2010 | Piran et al. ..................... 514/365 |

FOREIGN PATENT DOCUMENTS

| CN | 101648926 A | 2/2010 |
| CN | 101817801 A | 9/2010 |
| EP | 1 020 454 A1 | 7/2000 |
| EP | 2 398 784 B1 | 10/2012 |
| WO | 2010/144685 A1 | 12/2010 |

OTHER PUBLICATIONS

Shimadzu XRD-6000 manual. Published online 2008.*
Mino R. Caira, Crystalline Polymorphism of Orgainc Compounds, Topics in Current Chemistry, vol. 198, © Springer Verlag Berlin Heidelberg 1998, pp. 163-208.
Bernstein: Infrared Spectroscopy, Polymorphism in Molecular Crystals, Oxford, 2002, pp. 125-131.
Ivanisevic et al, Uses of X-Ray Powder Diffraction in the Pharmaceutical Industry, in Pharmaceutical Sciences Encyclopedia: Drug Discovery, Development, and Manufacturing, S.C. Gad (Ed.), John Wiley&Sons, 2010, pp. 1-42.
US Pharmacopoeia (USP 29), No. 941, X-Ray Diffraction, http://www.pharmacopoeia.cn/v29240/usp29nf24s0_c941.html, as retreived on Dec. 4, 2012.

* cited by examiner

*Primary Examiner* — Paul Zarek
*Assistant Examiner* — George W Kosturko
(74) *Attorney, Agent, or Firm* — Arent Fox LLP (57) ABSTRACT

The present invention relates to crystalline form I of Febuxostat as well as to pharmaceutical compositions comprising crystalline form I as an active pharmaceutical ingredient. Furthermore the present invention relates to a further polymorphic form of Febuxostat designated as form II and to a novel solvate of Febuxostat. The present invention also relates to methods of making crystalline form I, form II and the novel solvate of Febuxostat.

14 Claims, 8 Drawing Sheets

POLYMORPHS OF AN ACTIVE PHARMACEUTICAL INGREDIENT

FIELD OF THE INVENTION

The present invention relates to crystalline form I of Febuxostat as well as to pharmaceutical compositions comprising crystalline form I as an active pharmaceutical ingredient. Furthermore the present invention relates to a further polymorphic form of Febuxostat designated as form II and a novel solvate of Febuxostat. The present invention also relates to methods of making crystalline form I, form II and the novel solvate of Febuxostat.

BACKGROUND OF THE INVENTION

Febuxostat, 2-(3-cyano-4-isobutyloxy-phenyl)-4-methyl-5-thiazolecarboxylic acid regulates the biosynthesis of uric acid in vivo and is indicated for the use in the treatment of hyperuricemia and gout. It received marketing approval in EU (brand name Adenuric) and US (brand name Uloric) and is represented by the following general formula (I):

(I)

Specific crystal forms of Febuxostat designated as forms A, B, C, D and G are disclosed for example in EP 1020454.

Polymorphism is a phenomenon relating to the occurrence of different crystal forms for one molecule. There may be several different crystalline forms for the same molecule with distinct crystal structures and varying in physical properties like melting point. XRPD spectrum and IR-spectrum. These polymorphs are thus distinct solid forms which share the molecular formula of the compound from which the crystals are made up, however they may have distinct advantageous physical properties which can have a direct effect on the ability to process and/or manufacture the drug substance, like flowability, and the drug product, like flowability, as well as on drug product stability, dissolution, and bioavailability.

These distinct physical properties of different polymorphs of the same compound can render different polymorphs more, or less, useful for a particular purpose, such as for pharmaceutical formulation.

The crystal forms of Febuxostat disclosed for example in EP1020454, namely anhydrate A, anhydrate B, anhydrate C, hydrate G and a solvate with methanol (Form D) have certain drawbacks. The drawbacks of forms other than form A are explained in U.S. Pat. No. 7,361,676.

U.S. Pat. No. 7,361,676 discloses formulations comprising form A. In the comparative examples of said patent the drawbacks using known forms of Febuxostat others than form A are presented and explained in detail. The problems encountered with the non-A forms are, for example, polymorph conversion during formulation or stability studies resulting in non uniform dissolution. Polymorph A according to both references above is therefore the preferred solid state form of Febuxostat intended for formulation, however the solubility of form A is limited, as it has a value of 0.22 mg/ml.

Moreover, the preferred form A is difficult to make as form A is said to be obtainable in pure form only in a quite narrow window of temperature and methanol/water ratio in the region I as shown in FIG. 1 of EP1020454. The process to obtain pure form A is especially critical, as different polymorphic forms of Febuxostat are obtainable from the same solvent system.

Crystal forms of Febuxostat with both higher solubility and fewer problems with regard to polymorphic conversion during preparation and/or typical formulation conditions would facilitate the production of pharmaceutical compositions while at the same time more efficiently provide Febuxostat to a patient in need thereof. There is thus a need for solid forms of Febuxostat which avoid one or more problems of the known crystal forms.

SUMMARY OF THE INVENTION

The present invention relates to a new crystalline form of Febuxostat, which is now designated as form I, and pharmaceutical compositions comprising form I. The present invention also relates to new processes for the preparation of form I in which processes novel crystalline intermediates designated as form II of Febuxostat and a tert.-amylalcohol solvate of Febuxostat are employed for the preparation of form I of Febuxostat.

Crystalline form I of Febuxostat is stable as crystalline form I under a variety of conditions typically employed for the preparation of pharmaceutical compositions and upon storage. Moreover, form I has improved solid state properties, such as a high solubility in water, when compared to the available polymorphs of Febuxostat, in particular compared to the previously preferred form A of the prior art. Crystalline form I therefore is a highly valuable polymorph for the preparation of pharmaceuticals.

DETAILED DESCRIPTION OF THE INVENTION

As used herein, a "solvate" is a crystalline molecular compound in which molecules of the solvent are incorporated into the host lattice consisting of unsolvated molecules. A "hydrate" is a special kind of solvate, wherein the incorporated solvent is water. An "anhydrous" form is thus a form wherein no water molecules are incorporated into the host molecule crystal lattice.

The term "significant peaks" used herein and referring to XRD diffraction pattern generally means characteristic peaks as typically understood by a person skilled in the art for an XRD characterization. For example, "significant peaks" can be typically defined by having relative intensities to the most intense peak (intensity 100) of at least 10%, preferably of at least 20%, more preferably of at least 30%.

In a first aspect the present invention relates to a crystalline form of Febuxostat (hereinafter also referred to as form I).

Form I of Febuxostat can be characterized by an XRPD pattern comprising peaks at 2-theta angles of 6.6±0.2°, 12.8±0.2°, 24.5±0.2, 25.8±0.2° and 26.6±0.2°.

Preferably and notably, Form I of Febuxostat can be characterized by an XRD pattern as measured using CuKα radiation comprising significant peaks at 2-theta angles of 6.6±0.2°, 12.8±0.2°, 24.5±0.2°, 25.8±0.2° and 26.6±0.2°, and optionally further at 2-theta angle 23.8±0.2°.

Intensities used for the specification of Form I of Febuxostat above were all found to be greater than at least 10%, preferably greater than 20%, more preferably greater than 30% relative to the most intense peak for Form I of Febuxostat at 2-theta angles of 6.6±0.2°.

Alternatively form I of Febuxostat can alternatively be described by an IR spectrum comprising peaks at wavenumbers of 2960±2 $cm^{-1}$, 2874±2 $cm^{-1}$, 2535±2 $cm^{-1}$, 2229±2 $cm^{-1}$, 1673±2 $cm^{-1}$, 1605±2 $cm^{-1}$, 1509±2 $cm^{-1}$, 1422±2 $cm^{-1}$, 1368±2 $cm^{-1}$, 1323±2 $cm^{-1}$, 1274±2 $cm^{-1}$, 1166±2 $cm^{-1}$, 1116±2 $cm^{-1}$, 1045±2 $cm^{-1}$, 1013±2 $cm^{-1}$, 911±2 $cm^{-1}$, 820±2 $cm^{-1}$, 763±2 $cm^{-1}$ and 725±2 $cm^{-1}$.

The crystalline form I can be characterized as being an anhydrous form, that is its water content when stored at 20° C. at ambient pressure in an environment from 0% up to 90% relative humidity is below 0.1% according to Karl Fischer (KF), more preferably below 0.05% KF.

The present invention also relates to a process for the preparation of form I. Form I of Febuxostat may be prepared from crystalline form II, further described below, by a process comprising the step of:
a) heating crystalline form II to about 200° C.,
b) keeping crystalline form II at about 200° C. for a time sufficient to allow conversion into form I, and
c) recovering form I.

The transformation at about 200° C. is preferably carried out by keeping the temperature at that value for least one minute up to 1 hour, more preferably for 3 minutes to 30 minutes. For large amounts of crystalline form II to be converted these times may be increased so as to allow and assure complete conversion to form I. The skilled person will appreciate that conversion can be monitored, and completion of conversion determined, by XRPD measurements.

The term "about", used herein in connection with the indication of the transformation temperature, refers to a temperature range where crystal transformation takes place. As generally understood, it means that the transformation does not take place at an exact temperature, but rather reasonably around the indicated value, e.g. typically at temperatures±10° C. of the stated value, further noting that crystal transformation can be influenced not only by temperature but also by other ambient conditions such as humidity and pressure.

The present invention also provides an alternative process for the generation of form I comprising the steps of:
a) heating crystalline form II of Febuxostat to a temperature of at least 150° C., more preferably from 155° C. to 200° C.;
b) allowing vapor comprising Febuxostat to deposit onto a surface, in particular a surface having a temperature of below 150° C., more preferably of from −30° C. to 140° C., even more preferably of from 0° C. to 120° C., and
c) recovering form I of Febuxostat.

The present invention also relates to a crystalline form I of Febuxostat obtainable by either one of the alternative processes as defined above starting from form II of Febuxostat.

Surprisingly polymorph I of the invention shows better solubility compared to the known form A. The increase in solubility in an aqueous solution is approximately 20% (see example 3). Also surprisingly the kinetics of conversion to the known hemihydrate G in a mix of methanol and water is slower than the kinetics of the conversion of the of known anhydrate A to the known hemihydrate G, demonstrating improved polymorphic stability of novel form I.

The solvent system methanol/water represents a model for the dissolution of solid states of Febuxostat, with the hemihydrate G representing a thermodynamic very stable form with low solubility in aqueous systems.

As a further surprising advantage, the polymorph I of the invention is nonhygroscopic as shown by the moisture sorption/desorption experiment (see FIG. 3) and is therefore very suitable, for example for use in a wet granulation process for the production of pharmaceutical compositions comprising Febuxostat.

As a further surprising advantage polymorph I of Febuxostat is polymorphically very stable. It does not change its polymorphic state properties when stored for prolonged time e.g. under stress conditions, e.g. when stored at 40° C. for 3 months.

The crystal form I of Febuxostat of the invention as described above may advantageously be employed in various pharmaceutical formulations for use in the treatment of hyperuricemia and gout and related diseases in accordance with the present invention. The present invention therefore also relates to a pharmaceutical composition which comprises the crystalline form I of Febuxostat as described above and a pharmaceutically acceptable carrier.

The present invention therefore also relates to a pharmaceutical composition comprising the crystalline form I of Febuxostat, wherein form I is the only detectable crystalline form of Febuxostat, in particular the present invention relates to such pharmaceutical compositions, wherein more than 95% of the crystalline form I present in said composition is stably present as form I.

'Stably present' as defined herein means that even after storage of the pharmaceutical composition for 180 days, and preferably even after storage for 2 years, the crystalline form of Febuxostat designated as form I initially comprised in the pharmaceutical composition is still present as crystalline form I after storage for the indicated period.

The pharmaceutical compositions of the invention comprising the crystalline form I of Febuxostat may further comprise one or more pharmaceutically acceptable excipients which are preferably selected from the group consisting of fillers, sweeteners, buffering agents, glidants, flowing agents, flavouring agents, lubricants, preservatives, surfactants, wetting agents, binders, disintegrants and thickeners. Other excipients known in the field of pharmaceutical compositions may also be used. Furthermore, the pharmaceutical composition may comprise a combination of two or more excipients also within one of the members of the above mentioned group.

Examples of suitable excipients for pharmaceutical compositions of the invention comprising febuxostat are given in US2005/0043375A1, which is herein incorporated by reference, in paragraphs [0027] to [0030]. The excipients are typically contained in an amount of 50 to 98 parts by weight, and more preferably 60 to 95 parts by weight, based on 100 parts by weight of the solid preparation.

In paragraph [0028] US2005/0043375A1 discloses examples of the disintegrating agent for the pharmaceutical compositions of the present invention comprising febuxostat. The disclosed disintegrants, which can also be used for the pharmaceutical compositions of the present invention, include carmellose sodium, carmellose calcium, low-substituted hydroxypropyl cellulose, crosscarmellose sodium, carboxymethyl starch sodium and crosspovidone. Preferred disintegrants and preferred amounts for the disintegrating agent to be used in the pharmaceutical composition of the present invention are also disclosed in paragraph [0028] of US2005/0043375A1.

In paragraph [0029] US2005/0043375A1 discloses examples of additional excipients to be added in the preparation of pharmaceutical compositions comprising febuxostat, such as binders, lubricants, coating agents, plasticizers, diluents, colorants, preservatives, antiseptics or fragrance agents, which are also useful for the preparation of the pharmaceutical composition of the present invention.

In paragraph [0030] US2005/0043375A1 discloses examples of binders for the pharmaceutical composition of the present invention, such as hydroxypropyl cellulose, hydroxy propylmethyl cellulose, and polyvinyl pyrrolidone. The binder is contained in an amount of 0.5 to 25 parts by weight, and preferably 1 to 20 parts by weight, based on 100 parts by weight of the pharmaceutical composition of the present invention.

Examples of suitable processes for the preparation of the pharmaceutical compositions of the present invention are given in US2005/0043375A1, which is herein incorporated by reference, in paragraphs [0031] to [0033]. In summary the pharmaceutical compositions of the present invention are preferably solid preparations which can be produced by compressing a mixture of form I of the present invention with excipients and disintegrating agents. For example, one method for the production of the pharmaceutical composition of the present invention includes mixing form I of the present invention with suitable excipients in a suitable mixer. The mixture can then be directly compressed to tablets. Alternatively, a dry granulation step can be employed so as to produce granules suitable for tablet production. A wet granulation step can be employed to produce granules suitable for tablet production, in which step water, ethanol and solutions containing binders can be used.

Specific examples for the production of tablets of the present invention are given in US2005/0043375A1, paragraphs [0034] to [0048]. These examples can be repeated using form I of the present invention instead of the crystals of febuxostat referred to in US2005/0043375A1, paragraphs [0034] to [0048].

The pharmaceutical compositions of the invention comprising the crystalline form I of Febuxostat are preferably packaged or filled into containers. Containers are typically used for stable storage of the pharmaceutical compositions of the invention, for example at room temperature, such as at a temperature of about 20° C. to 30° C., e.g. at about 25° C., for a prolonged period, e.g. for at least 6 months, preferably at least about 24 months, e.g. for up to at least 24 months, e.g. for up to at least about 30 months, such as for up to about 60 months.

A preferred container is a bottle, in particular a glass bottle, having e.g. a screw closure, or is a blister, e.g. an aluminum blister or strip, e.g. a blister consisting of 2 aluminum foils or strips, or may be any other suitable container. More preferably said container is a gas-tight container, such as an air-tight container.

Preferred containers are glass bottles sealed with an aluminum membrane, alu-alu-blisters or strips. The container according to the invention is obtained by filling the pharmaceutical compositions of the invention into said container.

The present invention also relates to the use of crystalline form I of Febuxostat for the production of a pharmaceutical composition, in particular a pharmaceutical composition intended for sale in a tropical country having areas with an Af or Am climate according to the Koppen-Geiger climate classification.

In a second aspect, the present invention relates to a further novel form of Febuxostat (hereinafter referred to as form II).

Form II of Febuxostat can be characterized by an XRPD pattern comprising peaks at 2-theta angles of 2.9±0.2°, 5.8±0.2°, 12.0±0.2°, 12.3±0.2° and 25.2±0.2°.

Notably, Form II of Febuxostat can be characterized by an XRPD pattern as measured using CuKα radiation comprising the aforementioned peaks at 2-theta angles of 2.9±0.2°, 5.8±0.2°, 12.0±0.2°, 12.3±0.2° and 25.2±0.2° as significant peaks.

Intensities used for the specification of Form II of Febuxostat above were all found to be greater than at least 10% relative to the most intense peak for Form II of Febuxostat at 2-theta angles of 2.9±0.2°.

Alternatively form II of Febuxostat can be described by an IR spectrum comprising peaks at wavenumbers of 2960±2 $cm^{-1}$, 2874±2 $cm^{-1}$, 2537±2 $cm^{-1}$, 2229±2 $cm^{-1}$, 1684±2 $cm^{-1}$, 1656±2 $cm^{-1}$, 1605±2 $cm^{-1}$, 1510±2 $cm^{-1}$, 1428±2 $cm^{-1}$, 1371±2 $cm^{-1}$, 1326±2 $cm^{-1}$, 1280±2 $cm^{-1}$, 1173±2 $cm^{-1}$, 1115±2 $cm^{-1}$, 1043±2 $cm^{-1}$, 1008±2 $cm^{-1}$, 958±2 $cm^{-1}$, 915±2 $cm^{-1}$, 827±2 $cm^{-1}$, 765±2 $cm^{-1}$ and 725±2 $cm^{-1}$.

The present invention also relates to a process for the preparation of form II of Febuxostat comprising the steps of:
   a) dissolving Febuxostat in nitromethane;
   b) allowing form II of febuxostat to crystallize;
   c) recovering crystalline form II of Febuxostat from the solution; and
   d) optionally drying the form II crystals.

Typically any form of Febuxostat including amorphous Febuxostat is dissolved in nitromethane preferably at elevated temperature, e.g. at 40° C. up to the boiling point of the solvent whereas form II is formed upon cooling. In a preferred embodiment the solution is cooled to a temperature of 10° to −10° C., preferably +5° to 0° C. quickly, e.g. by placing the solution in an icebath.

Form II may be isolated by conventional methods, e.g. by filtration and drying, e.g. in vacuo. Form II of Febuxostat is stable under ambient laboratory conditions, e.g. it does not convert to another polymorphic form when stored e.g. at ambient temperature for 6 weeks.

Form II of Febuxostat is a valuable intermediate for the manufacture of form I of Febuxostat. Form II of Febuxostat may be transformed to form I of Febuxostat according to the processes disclosed for form I production above.

In a third aspect the present invention refers to a novel crystalline tert.-amylalcohol solvate of Febuxostat.

The novel crystalline tert.-amylalcohol solvate of Febuxostat can be characterized by an XRPD pattern comprising peaks at 2-theta angles of 6.1±0.2°, 8.6±0.2°, 11.4±0.2°, 17.3±0.2° and 25.3±0.2°.

Notably, the novel crystalline tert.-amylalcohol solvate of Febuxostat can be characterized by an XRPD pattern as measured using CuKα radiation comprising the aforementioned peaks at 2-theta angles of 6.1±0.2°, 8.6±0.2°, 11.4±0.2°, 17.3±0.2° and 25.3±0.2° as significant peaks.

Intensities used for the specification of the tert.-amylalcohol solvate of Febuxostat above were all found to be greater than 10% relative to the most intense peak for the tert.-amylalcohol solvate of Febuxostat at 2-theta angles of 6.1±0.2°.

The tert.-amylalcohol solvate of Febuxostat contains about 0.4 mol to 0.6 mol of tert.-amylalcohol. TGA shows for example a mass loss of about 13.2% corresponding to 0.55 mol tert.-amylalcohol per mol of Febuxostat.

In another embodiment the present invention therefore relates to a process for the preparation of the tert.-amylalcohol solvate of Febuxostat comprising the step of:
a) dissolving Febuxostat in tert.-amylalcohol;
b) concentrating the solution of step a) by evaporating the solvent, thereby allowing the tert.-amylalcohol solvate of Febuxostat to crystallize; and
c) recovering the tert.-amylalcohol solvate of Febuxostat.

The amount of tert.-amylalcohol in the process for the preparation of the novel solvate is not critical, however a solution of Febuxostat in tert.-amylalcohol has to be ensured, optionally with the help of a filtration step.

The tert.-amylalcohol solvate is stable, e.g. when stored under ambient conditions in open atmosphere for several weeks, e.g. for 5 weeks.

The present invention also relates to a process for the preparation of form I of Febuxostat from the tert.-amylalcohol solvate of Febuxostat comprising the steps of:
a) heating the tert.-amylalcohol solvate of Febuxostat; and
b) recovering form I of Febuxostat.

The tert-amylalcohol solvate of Febuxostat is a valuable intermediate for the manufacture of form I of Febuxostat. The tert.-amylalcohol solvate of Febuxostat may be transformed to form I of Febuxostat according to the process disclosed for form I production starting from tert.-amylalcohol solvate of Febuxostat above.

Typically the tert.-amylalcohol solvate is heated to a temperature range of 130° C. to 180° C., preferably to 140° C. to 160° C. for a certain period of time. Typically dependent on the temperature several minutes to several hours are required to complete the transformation, e.g. at a temperature of about 150° C. the transformation is complete in less than 6 hours. The transformation may be monitored by classical methods, e.g. XRPD analysis. At lower temperatures, a desolvated intermediate is formed.

The present invention also relates to a crystalline form I of Febuxostat obtainable by the process as defined above starting from the tert.-amylalcohol solvate of Febuxostat.

Other objects, features, advantages and aspects of the present invention will become apparent to those of skill from the following description. It should be understood, however, that the description and the following specific examples, while indicating preferred embodiments of the invention, are given by way of illustration only. Various changes and modifications within the spirit and scope of the disclosed invention will become readily apparent to those skilled in the art from reading the description and the other parts of the present disclosure.

EXAMPLES

XRPD patterns were obtained with an X'Pert PRO diffractometer (PANalytical, Almelo, The Netherlands) equipped with a theta/theta coupled goniometer in transmission geometry, programmable XYZ stage with well plate holder. CuKα radiation source (CuKα$_{1,2}$; wavelength 0.15419 nm) with a focusing mirror, a 0.5° divergence slit, a 0.02° soller slit collimator and a 1° anti-scattering slit on the incident beam side, a 2 mm anti-scattering slit, a 0.02° soller slit collimator and a Nickel filter on the diffracted beam side and a solid state PIXcel detector. The patterns were recorded at a tube voltage of 40 kV, tube current of 40 mA, applying a stepsize of 0.013° 2-theta with 80 s per step in the angular range of 2° to 40° 2-theta.

The IR spectra were collected on a MKII Golden Gate™ Single Reflection Diamond ATR (attenuated total reflection) cell with a Bruker Tensor 27 FTIR spectrometer with 4 cm$^{-1}$ resolution at ambient conditions. To collect a spectrum a spatula tip of a sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of about ±2 cm$^{-1}$. Thus, an infrared peak that appears at 1716 cm$^{-1}$ can appear between 1714 and 1718 cm$^{-1}$ on most infrared spectrometers under standard conditions.

Figure 5:
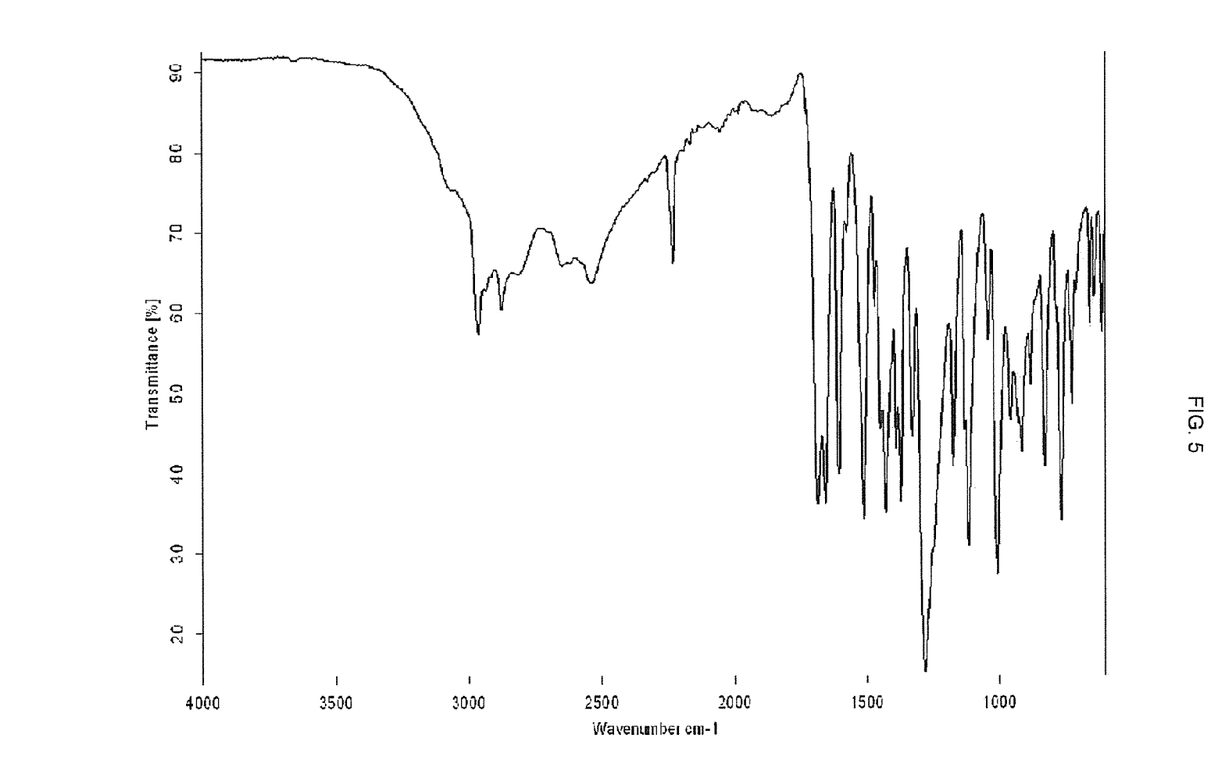
FIG. 5: IR spectrum of Form II of Febuxostat
Figure 6:
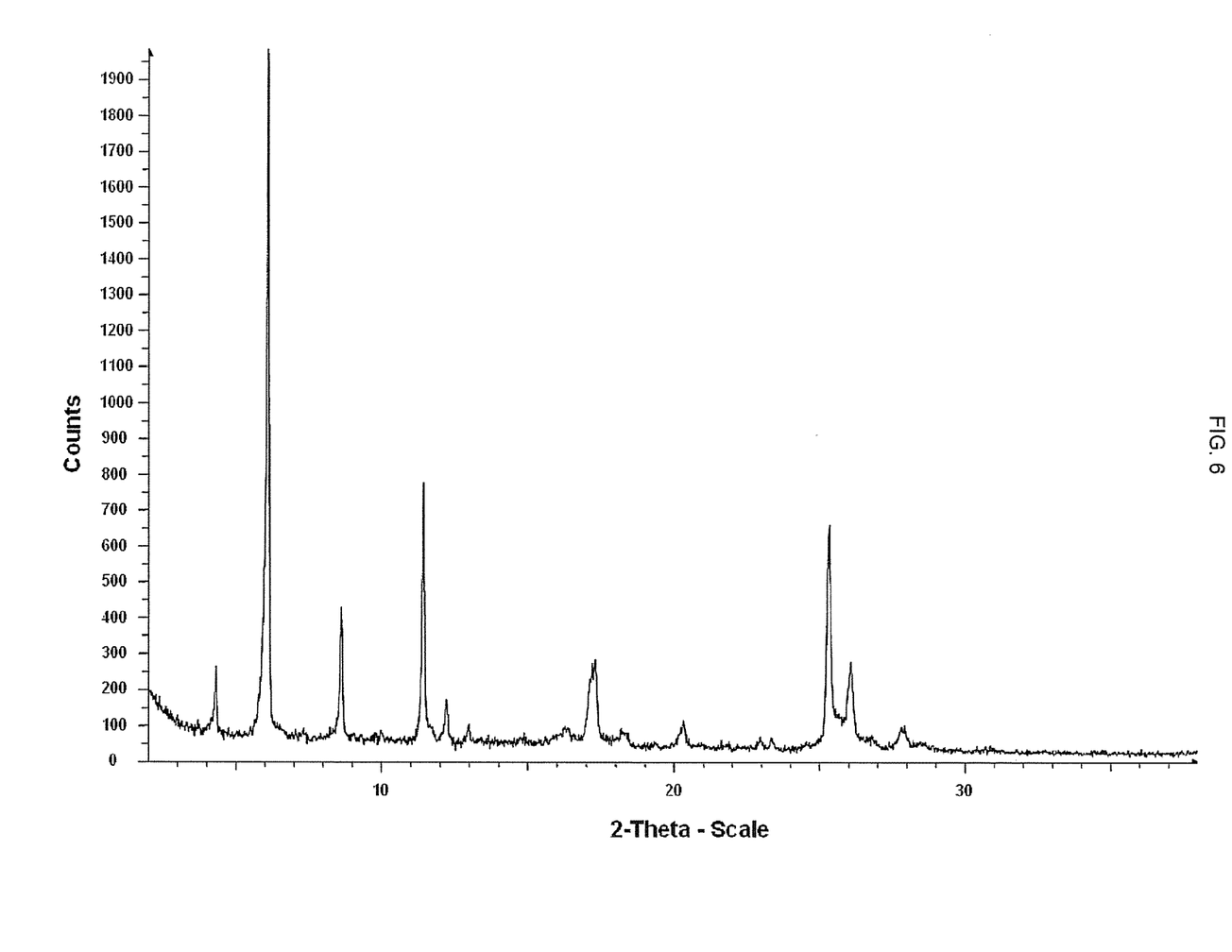
FIG. 6: XRPD pattern of the tert.-amylalcohol solvate of Febuxostat
Figure 7:
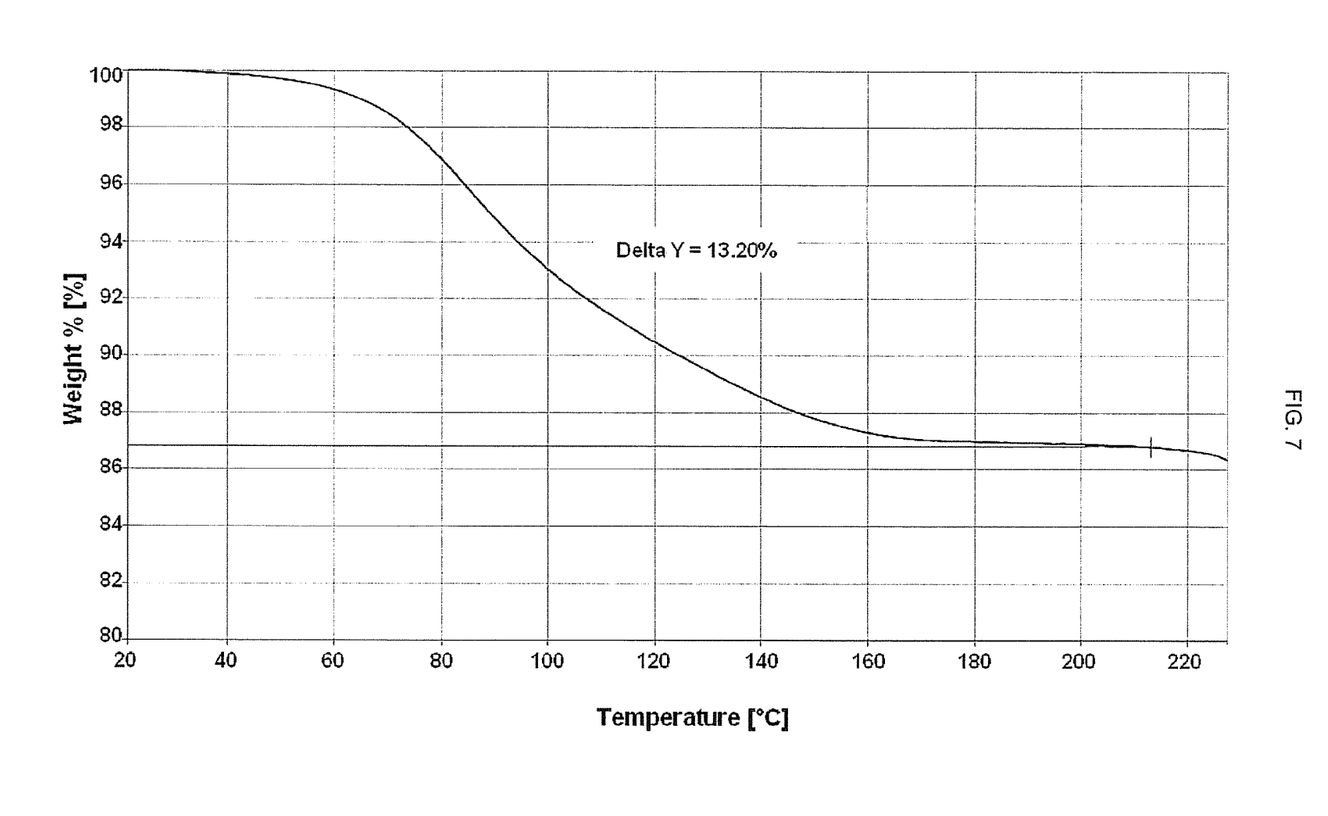
FIG. 7: TGA curve of the tert.-amylalcohol solvate of Febuxostat

TGA's were performed with Thermogravimetric-system TGA-7, Pyris-Software for Windows NT, (Perkin-Elmer, Norwalk, Conn., USA), Platinum-sample holder (50 μl), Nitrogen as the purge gas (Sample purge: 20 ml/min, balance purge: 40 ml/min). Heating rate: 10° C./min;

The moisture sorption/desorption isotherms were recorded with a SPS-11 moisture sorption analyzer (MD Messtechnik, Ulm, D). In the experiment displayed in FIG. 5 the measurement cycle was started at 0% RH increased in 10% steps up to 90% RH, decreased in 10% steps down to 0% RH, increased in 10% steps up to 90% RH and finally decreased in 10% steps down to 0% RH. In the experiments displayed in FIG. 8 and FIG. 9 the measurement cycle was started at 0% RH, increased in 10% steps up to 90% RH and decreased in 10% steps down to 0% RH. The equilibrium condition for each step was set to a mass constancy of ±0.01% over 30 min. The temperature was 25±0.1° C.

Example 1

Preparation of Febuxostat Form II 1.0 g of form A of 2-(3-cyano-4-isobutyloxyphenyl)-4-methyl-5-thiazolecarboxylic acid (Febuxostat) were dissolved in 120 ml nitromethane upon heating to 75° C. The clear solution was filtered through 0.44 μm milipore filter. The solution was then quickly cooled in an icebath and the suspension was stirred in the icebath for further 30 min. The crystals were filtered off and dried in vacuo for 3 h at about 60 mbar.

Yield: 820 mg

TABLE 1

XRPD angles 2-theta, relative intensities of form II of Febuxostat

| angle [2-Theta]° | rel intensity [%] |
|---|---|
| 2.89 | 100 |
| 4.07 | 5 |
| 5.83 | 14 |
| 7.36 | 5 |
| 7.87 | 5 |
| 8.76 | 6 |
| 10.17 | 5 |
| 11.99 | 14 |
| 12.26 | 34 |
| 13.40 | 7 |
| 14.64 | 5 |
| 17.47 | 6 |
| 17.83 | 6 |
| 23.73 | 5 |
| 24.34 | 12 |

TABLE 1-continued

XRPD angles 2-theta, relative intensities of form II of Febuxostat

| angle [2-Theta]° | rel intensity [%] |
|---|---|
| 25.22 | 17 |
| 26.01 | 7 |
| 27.28 | 5 |
| 29.47 | 3 |
| 29.78 | 2 |

Form II of Febuxostat can be classified as non hygroscopic. Moisture sorption/desorption analysis showed no significant water uptake up to a relative humidity of 90%. TGA and DSC confirms the presence of an unsolvated respectively anhydrous form.

Example 2

Preparation of Form I of Febuxostat from Form II of Febuxostat

Form II of Febuxostat was heated at a heating rate of 10° K/min to about 205° C. At high temperature, a new crystalline form was identified. The sample showed a melting point of 209° C. to 210° C., the melting point of form I. Form I was characterized by XRPD.

TABLE 2

XRPD angles 2-theta, relative intensities of form I of Febuxostat

| angle [2-Theta]° | rel intensity [%] |
|---|---|
| 3.26 | 14 |
| 6.60 | 100 |
| 7.10 | 18 |
| 7.62 | 16 |
| 7.96 | 10 |
| 12.75 | 92 |
| 13.26 | 16 |
| 13.60 | 9 |
| 16.27 | 27 |
| 16.80 | 11 |
| 18.04 | 5 |
| 19.76 | 9 |
| 19.98 | 13 |
| 21.11 | 11 |
| 21.77 | 13 |
| 22.21 | 8 |
| 23.84 | 35 |
| 24.51 | 61 |
| 25.82 | 66 |
| 26.29 | 15 |
| 26.59 | 36 |
| 27.63 | 8 |
| 28.06 | 12 |
| 28.91 | 4 |
| 30.54 | 6 |
| 32.01 | 4 |

Example 3

Solubility Determination of Form I and form A 25 mg of Febuxostat form I or form A, obtained according to the procedure described in EP1020454 were stirred in a mixture of 20 ml of methanol and water (1:1 v/v). 1 ml of the suspension was withdrawn from each suspension within a time range of 5 to 180 min with the aid of a volumetric pipette and filtered. The filtrate was diluted to 25 ml with a 50% (v/v) methanol/water mixture and the concentration was determined by UV-spectrophotometry at 314 nm (apparatus: Shimadzu UV 1800).

Figure 8:
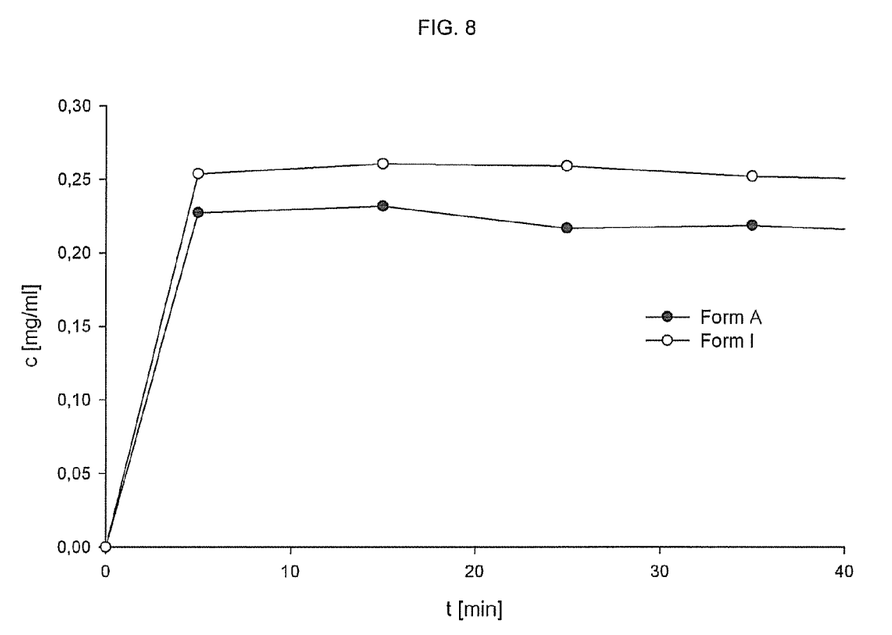
FIG. 8: Comparison of the solubility of form I with form A in MeOH/$H_2O$ (50%:50% v/v)

A calibration curve was determined based on a series of known concentrations in the same solvent system. The results are shown in FIG. 8:

FIG. 8 demonstrates that the solubility of form I exceeds the solubility of form A by approximately 20%.

Example 4

Preparation of the Tert.-amylacohol Solvate of Febuxostat 200 mg of 2-(3-cyano-4-isobutyloxyphenyl)-4-methyl-5-thiazolecarboxylic acid (Febuxostat) were dissolved in 10 ml of tert.-amylalcohol and heated up to 65° C. After filtration of the clear solution (0.44 µm milipore filter), the solvent was allowed to evaporate under open atmosphere.

Yield: 220 mg

TABLE 3

XRPD angles 2-theta, relative intensities of the tert.-amylalcohol solvate of Febuxostat

| Angle [2-Theta]° | rel Intensity [%] |
|---|---|
| 4.30 | 13 |
| 6.08 | 100 |
| 8.62 | 22 |
| 11.42 | 39 |
| 12.21 | 9 |
| 12.95 | 5 |
| 16.26 | 5 |
| 17.30 | 14 |
| 18.34 | 4 |
| 20.32 | 6 |
| 22.97 | 3 |
| 23.38 | 3 |
| 25.34 | 33 |
| 26.09 | 14 |
| 27.89 | 4 |

Example 5

Preparation of Form I of Febuxostat from the Tert.-amylalcohol Solvate of Febuxostat 200 mg of Cert.-amylalcohol solvate of Febuxostat were stored at 150° C. for 5 hours.

Yield: 140 mg

The product was analyzed by PXRD and was found to be pure form I.

The invention claimed is:

1. A crystalline Form I of Febuxostat having an X-ray powder diffraction pattern as measured using CuKα radiation comprising peaks at 2-theta angles of 6.6±0.2°, 12.8±0.2°, 24.5±0.2, 25.8±0.2°, 26.6±0.2°, and being characterized by an IR spectrum comprising absorption bands at wavenumbers of about 2960±2 cm$^{-1}$, 2874±2 cm$^{-1}$, 2535±2 cm$^{-1}$, 2229±2 cm$^{-1}$, 1673±2 cm$^{-1}$, 1605±2 cm$^{-1}$, 1509±2 cm$^{-1}$, 1422±2 cm$^{-1}$, 1368±2 cm$^{-1}$, 1323±2 cm$^{-1}$, 1274±2 cm$^{-1}$, 1166±2 cm$^{-1}$, 1116±2 cm$^{-1}$, 1045±2 cm$^{-1}$, 1013±2 cm$^{-1}$, 911±2 cm$^{-1}$, 820±2 cm$^{-1}$, 763±2 cm$^{-1}$ and 725±2 cm$^{-1}$.

Figure 1:
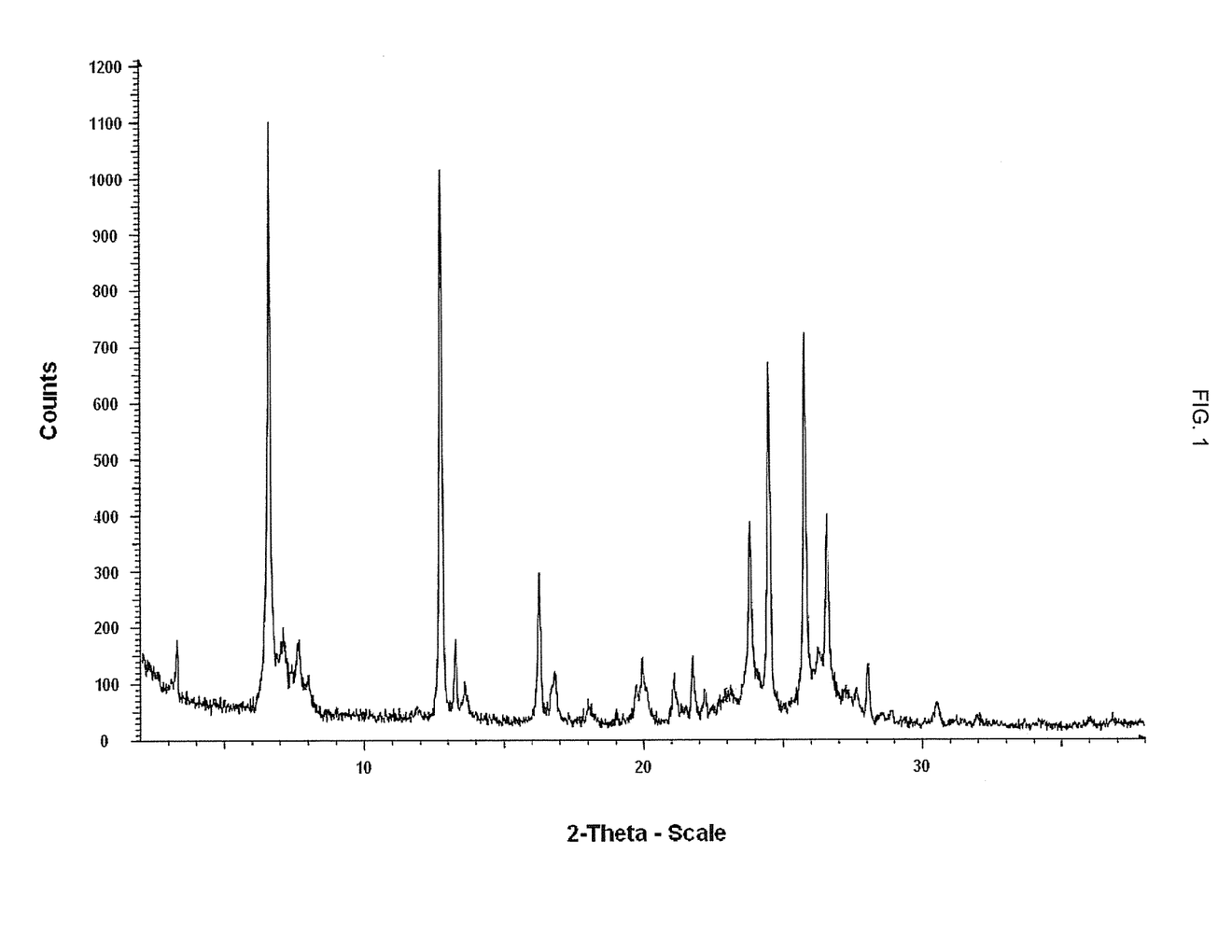
FIG. 1: XRPD pattern of form I of Febuxostat
Figure 2:
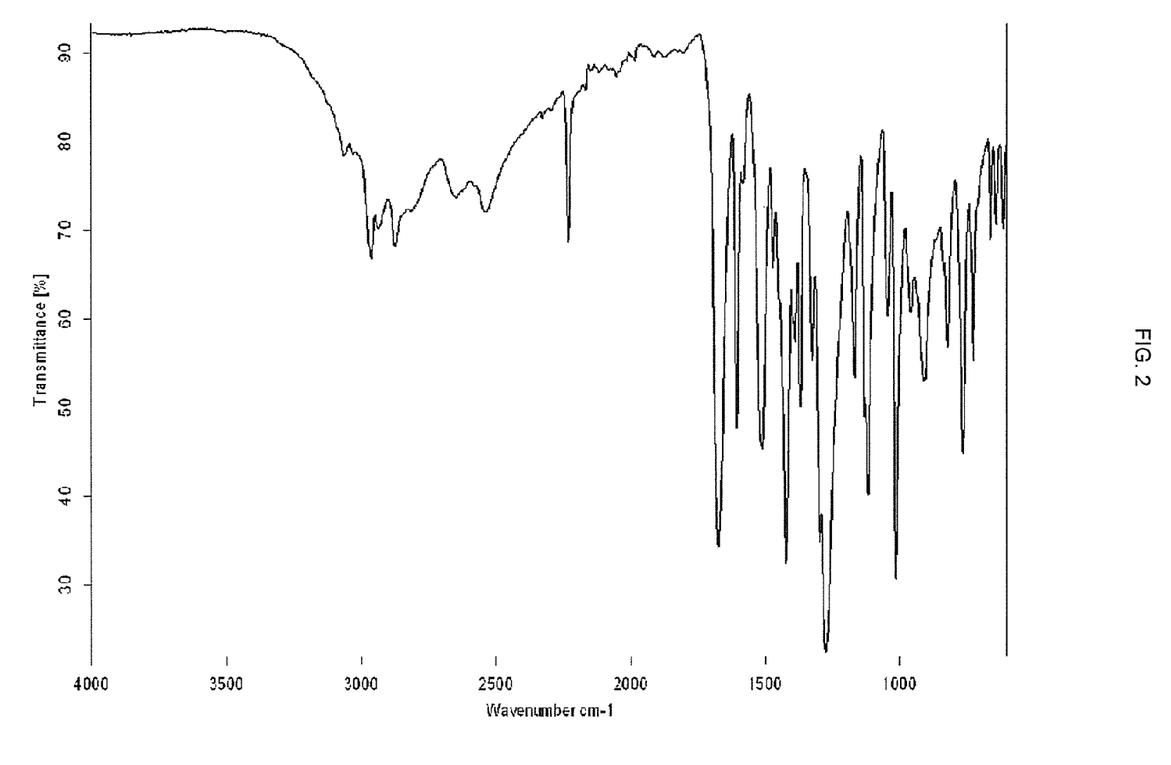
FIG. 2: IR spectrum of form I of Febuxostat
Figure 3:
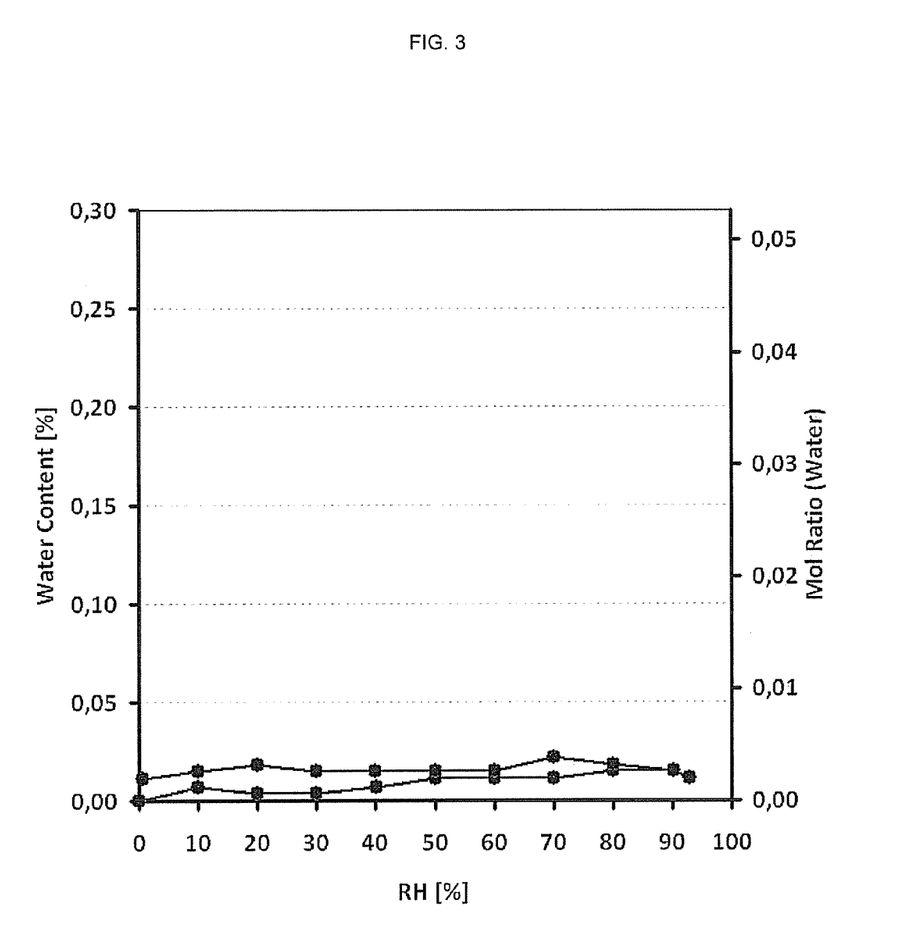
FIG. 3: Dynamic moisture sorption/desorption curve of form I of Febuxostat
Figure 4:
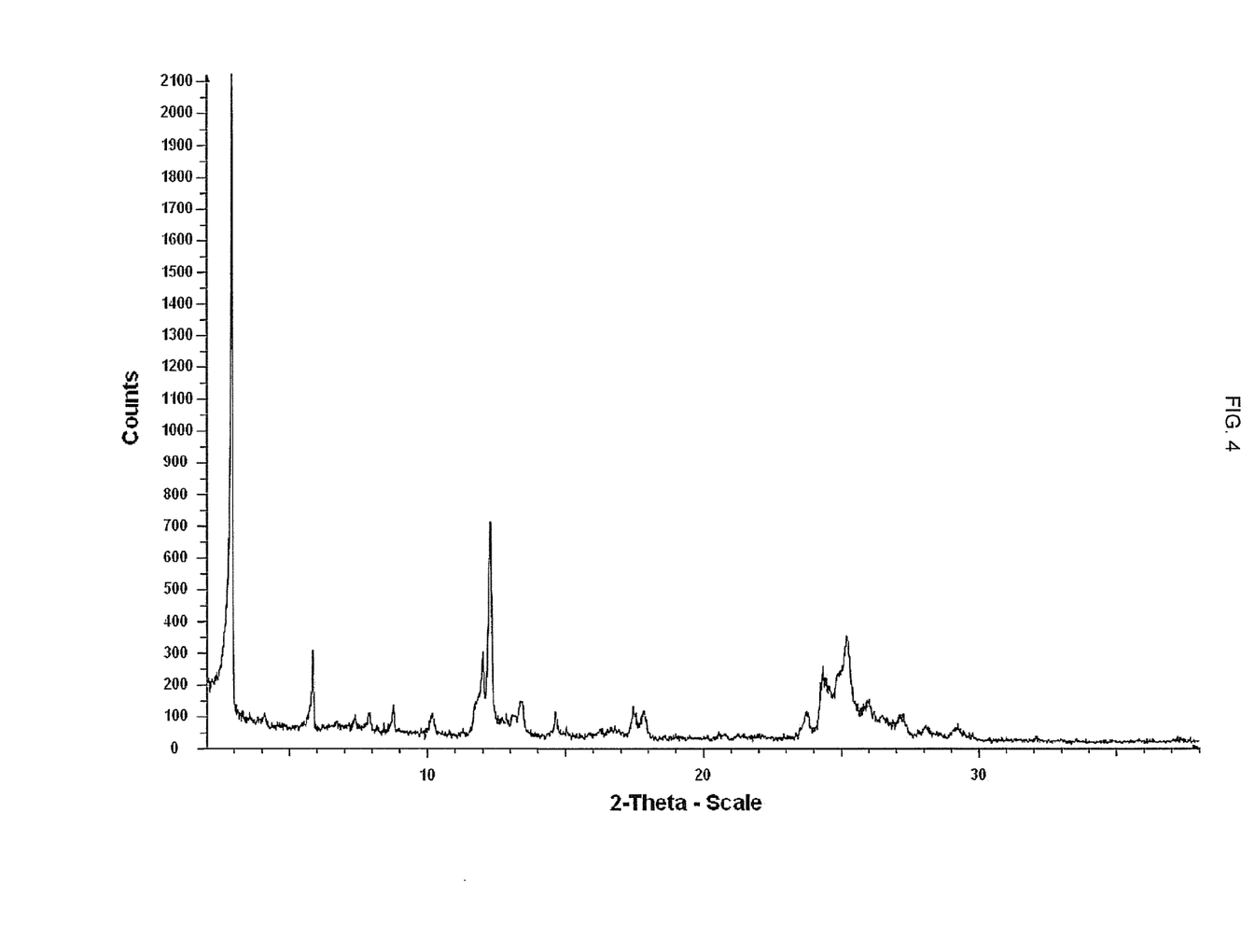
FIG. 4: XRPD pattern of form II of Febuxostat

2. The crystalline form of Febuxostat according to claim 1 characterized by a moisture sorption/desorption curve as shown in FIG. 3.

3. A pharmaceutical composition comprising a crystalline form of Febuxostat according to claim 1, further comprising at least one pharmaceutically acceptable excipient.

4. The pharmaceutical composition according to claim 3, which is an oral dosage form.

5. A process for the production of a pharmaceutical composition according to claim 3, comprising the step of mixing a crystalline form of Febuxostat according to claim 1 with a pharmaceutically acceptable excipient.

6. A process for the preparation of Form I of Febuxostat defined above by claim 1 comprising the steps of:
   either
   a-1) heating crystalline Form II of Febuxostat characterized by an X-ray powder diffraction pattern as measured using CuKα radiation comprising peaks at 2-theta angles of 2.9±0.2°, 5.8±0.2°, 12.0±0.2°, 12.3±0.2° and 25.2±0.2° to about 200° C.,
   b-1) keeping crystalline Form II at about 200° C. for at least one minute to allow conversion into Form I, and
   c-1) recovering Form I;
   or
   a-2) heating crystalline Form II of Febuxostat characterized by an X-ray powder diffraction pattern as measured using CuKα radiation comprising peaks at 2-theta angles of 2.9±0.2°, 5.8±0.2°, 12.0±0.2°, 12.3±0.2° and 25.2±0.2° to a temperature of at least 150° C.;
   b-2) allowing vapor comprising Febuxostat to deposit onto a surface, and
   c-2) recovering Form I of Febuxostat;
   or
   a-3) heating a tert-amylalcohol solvate of Febuxostat characterized by an X-ray powder diffraction pattern as measured using CuKα radiation with peaks at 2-theta angles of 6.1±0.2°, 8.6±0.2°, 11.4±0.2°, 17.3±0.2° and 25.3±0.2°; and
   b-3) recovering Form I of Febuxostat.

7. A method of treatment of hyperuricemia and/or gout comprising administering to a patient in need of such treatment the pharmaceutical composition as defined in claim 3.

8. The pharmaceutical composition according to claim 3, which is a capsule or a tablet.

9. The process for the preparation of Form I of Febuxostat according to claim 6, wherein in step a-2) the temperature for heating crystalline form II of Febuxostat, is from 155° C. to 200° C.

10. The process for the preparation of Form I of Febuxostat according to claim 6, wherein in step b-2) said surface has a temperature of below 150° C.

11. The process for the preparation of Form I of Febuxostat according to claim 6, wherein in step b-2) said surface has a temperature of from −30° C. to 140° C.

12. The process for the preparation of Form I of Febuxostat according to claim 6, wherein in step b-2) said surface has a temperature of from 0° C. to 120° C.

13. The process according to claim 6, wherein Form II of Febuxostat in step a-1) or step a-2) was obtained by a process comprising the steps of:
   a) dissolving Febuxostat in a solution of nitromethane;
   b) allowing Form II of Febuxostat to crystallize;
   c) recovering crystalline Form II of Febuxostat from the solution; and
   d) optionally drying the crystalline Form II of Febuxostat.

14. The process according to claim 6, wherein the tert-amylalcohol solvate of Febuxostat of step a-3) was obtained by a process comprising the steps of:
   a) dissolving Febuxostat in a solution of tert-amylalcohol;
   b) concentrating the solution of step a) by evaporating the solution of Febuxostat and tert-amylalcohol, thereby allowing the tert-amylalcohol solvate of Febuxostat to crystallize; and
   c) recovering the tert-amylalcohol solvate of Febuxostat.

* * * * *

UNITED STATES PATENT AND TRADEMARK OFFICE
CERTIFICATE OF CORRECTION

PATENT NO. : 8,946,441 B2  
APPLICATION NO. : 13/702077  
DATED : February 3, 2015  
INVENTOR(S) : Andreas Hotter Page 1 of 1

It is certified that error appears in the above-identified patent and that said Letters Patent is hereby corrected as shown below:

Title page PCT No. should read:

Item (86) PCT No.: PCT/EP2011/060630

Signed and Sealed this  
Nineteenth Day of May, 2015

Michelle K. Lee  
*Director of the United States Patent and Trademark Office*